US010376540B2

(12) United States Patent
Canals Almazán et al.

(10) Patent No.: US 10,376,540 B2
(45) Date of Patent: Aug. 13, 2019

(54) TUNGSTEN (VI) SALTS USED TO TREAT INFERTILITY, FOR STIMULATING FERTILITY AND NORMAL REPRODUCTION IN A NON-DIABETIC FEMALE MAMMAL, AND FOR IMPROVING THE EFFECTIVENESS OF ASSISTED REPRODUCTION TECHNIQUES

(71) Applicant: OXOLIFE, S.L., Sant Quirze del Vallés (ES)

(72) Inventors: Ignacio Canals Almazán, Sant Quirze del Vallés (ES); Agnès Arbat Bugié, Sant Quirze del Vallés (ES)

(73) Assignee: OXOLIKE, S.L., Sant Quirze del Vallés (ES)

( * ) Notice: Subject to any disclaimer, the term of this patent is extended or adjusted under 35 U.S.C. 154(b) by 0 days.

(21) Appl. No.: 15/327,292

(22) PCT Filed: Jul. 21, 2014

(86) PCT No.: PCT/ES2014/070586
§ 371 (c)(1),
(2) Date: Jan. 18, 2017

(87) PCT Pub. No.: WO2016/012632
PCT Pub. Date: Jan. 28, 2016

(65) Prior Publication Data
US 2017/0173074 A1  Jun. 22, 2017

(51) Int. Cl.
| | |
|---|---|
| *A23L 2/52* | (2006.01) |
| *A61K 9/20* | (2006.01) |
| *A61K 9/28* | (2006.01) |
| *A61K 9/48* | (2006.01) |
| *A23L 33/16* | (2016.01) |
| *A61K 33/24* | (2019.01) |
| *A61K 33/30* | (2006.01) |
| *A61P 15/08* | (2006.01) |
| *C01G 41/00* | (2006.01) |
| *C01G 41/02* | (2006.01) |

(52) U.S. Cl.
CPC .............. *A61K 33/24* (2013.01); *A23L 2/52* (2013.01); *A23L 33/16* (2016.08); *A61K 9/20* (2013.01); *A61K 9/28* (2013.01); *A61K 9/48* (2013.01); *A61K 33/30* (2013.01); *A61P 15/08* (2018.01); *C01G 41/00* (2013.01); *C01G 41/02* (2013.01); *A23V 2002/00* (2013.01)

(58) Field of Classification Search
CPC ............ A61K 33/24; A61K 9/28; A61K 9/48; A61K 33/30; A61K 9/20; C01G 41/02; C01G 41/00; A23L 33/16; A23L 2/52; A23V 2002/00; A61P 15/08
See application file for complete search history.

(56) References Cited

U.S. PATENT DOCUMENTS

| | | | | |
|---|---|---|---|---|
| 4,328,134 | A | * 5/1982 | Schally | ................ C07K 5/0825 525/54.11 |
| 7,122,209 | B2 | * 10/2006 | Gomis De Barbara | ..................... A61K 33/24 424/617 |
| 9,675,638 | B2 | 6/2017 | Canals Almazan et al. | |
| 2004/0131697 | A1 | 7/2004 | Gomis De Barbara et al. | |
| 2006/0100154 | A1 | * 5/2006 | Koch | ..................... A61K 38/09 514/9.9 |
| 2008/0206356 | A1 | 8/2008 | Guinovart Cirera et al. | |

FOREIGN PATENT DOCUMENTS

ES        2108642 A1    12/1997

OTHER PUBLICATIONS

U.S. Appl. No. 14/762,603, filed Jul. 22, 2015, now U.S. Pat. No. 9,675,638, Issued.
Agarwal et al. Oxidative stress and its implications in female infertility—a clinician's perspective. Reprod. BioMed. Online. Nov. 2005;11(5):641-50.
Ballester et al., Tungstate administration improves the sexual and reproductive function in female rats with streptozotocin-induced diabetes. Hum. Reprod. Aug. 2007;22(8):2128-35.
Burks et al., IRS-2 pathways integrate female reproduction and energy homeostasis. Nature. Sep. 21, 2000;407 (6802):377-82.
González et al., Genetic manipulation of IRS proteins: animal models for understanding the molecular basis of diabetes. Avences en Diabetologia. 2009;25(1):21-26.
Jin, Effect of obesity on reproductive function and improvement of weight loss on reproductive function of woman with obesity but no ovulation. Medicine Health Sciences of Chinese Master's Theses, Full-text Database, E065-103. 11 pages.
Kubota et al., Disruption of insulin receptor substrate 2 causes type 2 diabetes because of liver insulin resistance and lack of compensatory beta-cell hyperplasia. Diabetes. Nov. 2000;49(11):1880-9.
Sharma et al., Female Infertility: An Overview. IJPSR. 2011;2(1):1-12.
Vause et al., Ovulation induction in polycystic ovary syndrome: JOGC. No. 242, May 2010. pp. 495-502.
Withers et al., Disruption of IRS-2 causes type 2 diabetes in mice. Nature. Feb. 26, 1998;391(6670):900-4.
International Search Report for Application No. PCT/EP2014/051141, dated May 5, 2014.
International Search Report for Application No. PCT/ES2014/070586, dated Mar. 27, 2015.

* cited by examiner

*Primary Examiner* — Snigdha Maewall
(74) *Attorney, Agent, or Firm* — McCarter & English, LLP; Jill Mello

(57) ABSTRACT

The invention relates to tungsten (VI) salts for use thereof in the treatment of infertility in a non-diabetic female mammal, for favoring normal reproduction and fertility in a non-diabetic female mammal, or for increasing the efficacy of an assisted reproductive technique applied to a mammal, as well as compositions containing same and methods for treatment using same.

18 Claims, No Drawings

TUNGSTEN (VI) SALTS USED TO TREAT INFERTILITY, FOR STIMULATING FERTILITY AND NORMAL REPRODUCTION IN A NON-DIABETIC FEMALE MAMMAL, AND FOR IMPROVING THE EFFECTIVENESS OF ASSISTED REPRODUCTION TECHNIQUES

RELATED APPLICATIONS

This application is a 35 U.S.C. § 371 national stage filing of International Application No. PCT/ES2014/070586, filed on Jul. 21, 2014, the entire contents of which are incorporated herein by reference.

The present invention relates to tungsten (VI) salts and compositions containing same, for use thereof in the treatment of infertility, for favoring normal reproduction and fertility in a non-diabetic female mammal, as well as for improving the efficacy of an assisted reproductive technique applied to a mammal.

PRIOR ART

Fertility in mammals is a multistage process that is not totally efficient naturally. Factors such as age, eating habits or life style, among others, modulate the success of this process. In this sense, it is known for example that pregnancy rate in women 20 to 24 years of age is about 86%, while it diminishes to 50% in women 35 to 32 years of age [*Management of the Infertile Woman* by Helen A. Carcio; *The Fertility Sourcebook* by M. Sara Rosenthal, *ASAS Summary of FAIR* 2012]. Other factors such as overweight or underweight are also responsible for delays in achieving pregnancy naturally or even for the impossibility in achieving same [*Fertil Steril* 2013; 100:631-7]. It is estimated that about 66% of couples do not conceive naturally during the first 3 months of unprotected sexual intercourse. This figure decreases to 15% of couples in the course of the first year of unprotected sexual intercourse. Infertility is defined (WHO, ASRM, NICE) as the inability to conceive after 12 months of regular, unprotected sexual intercourse. The term "subfertility" has also been coined, particularly in Europe, to define those couples with any form or degree of reduced fertility leading to delay in conception [Gnoth C et al *Definition and prevalence of subfertility and infertility, Human reproduction* 2005; 20(5):1144-1147].

The main causes of infertility among women include ovulatory dysfunctions, pathologies of the reproductive tract, reduced oocyte quality and follicular depletion inherent to aging. However, there is also a considerable percentage of women with unexplained infertility, also referred to as idiopathic infertility, one of the possible causes of which relates to deficiencies in the implantation process.

Follicular development, ovulation, migration of immature egg (oocyte), as well as subsequent conception and zygote implantation on the uterine wall is regulated by hormonal secretions of certain endocrine organs such as the pituitary gland, the hypothalamus and the thyroid gland, for example. Among the different biological causes of infertility in women, causes linked to disorders in the hormonal stimuli regulating this whole process can also be pointed out.

Different treatments for female infertility including, among others, the administration of medicinal products for treating hormonal problems involving ovulation disruption (such as, clomiphene citrate or gonadotropins, for example), are known. Likewise, some beneficial effects have been postulated with various treatments based on taking vitamin supplements, particularly vitamin B, vitamin C, vitamin E and folic acid, mineral supplements such as selenium, zinc or iron complexes or salts, essential fatty acids (omega-3), as well as extracts from plants such as chaste tree (*Vitex agnus-castus*), damiana, licorice, red clover flower, chasteberry, black cohosh, dong quai (*Angelica sinensis*), wild yam or sweet potato (*Dioscorea villosa*), false unicorn root, green tea, nettles (*Urtica dioica*), wild oats (*Avena sativa*), dandelion (*Taraxacum officinale*), etc., although the efficacy has not been clearly demonstrated in any of these treatments.

The percentage of pregnancies achieved by means of the aforementioned treatments has limitations. In this sense, for example, it has been observed that treatment of women with irregular or no ovulation by means of administering clomiphene citrate, a drug of the stilbene family, allows restoring ovulation in a high percentage, but the pregnancy rate remains low, equal to or less than about 50%.

In vitro fertilization treatments are very effective in the oocyte fertilization step. However, the embryo implantation rate on the uterine wall is low. This promotes multiple embryo transfers per each in vitro fertilization cycle, with the consequence of a higher percentage of risky multiple pregnancies.

Finally, it is known that metabolic disorders such as diabetes or obesity entail a limitation of fertility. It is known that partial or complete recovery of glycemia, insulinemia and/or body weight in diabetic or obese female mice with damaged reproductive function, involves an improvement in fertility.

Different pharmacological treatments, such as metformin or tungsten (VI) salts, or even life style changes, have been shown to improve diabetes or insulin disorders, such as insulin deficiency or insulin resistance, for example, completely or partially recovering the reproductive function, when the infertility is due to diabetes or insulin disorders.

In the specific case of sodium tungstate, it is known that rats with diabetes and insulinopenia induced by the injection of streptozotocin partially recover circulating insulin levels after a prolonged treatment (10 weeks) with sodium tungstate as a result of partially reversing diabetes. Subsequently, when the female rats partially recovered from diabetes mate with healthy male rats, it is observed that, parallel to the partial recovery from diabetes, they have partially recovered their reproductive capacity. Particularly, it is observed that the percentage of births with respect to the number of positive curettages in female mice which had partially recovered from diabetes after treatment with sodium tungstate increases to 66%, a percentage which is lower than non-diabetic female mice where the percentage is 100%. (cf. J. Ballester et. al., "Tungstate administration improves the sexual and reproductive function in female rats with streptozotocin-induced diabetes", Human Reproduction, 2007, vol. 22, pp. 2128-2135). Nevertheless, the tungsten (VI) salts were neither observed nor postulated to have effect on non-diabetic female animals.

Tungsten is found in trace amounts in animals and plants. For example, tungsten content of up to a maximum of 100 mg/kg has been described in plants [Gbaruko B. C. & Igwe J. C. *Global Tungsten: Occurrence, Chemistry, Environmental and Health Exposure Issues. Journal of Environmental Research* 2007; 1(1):27-32].

In view of the foregoing, despite the extensive research and progress in understanding and handling the reproductive process in mammals and particularly in humans, there are still many couples who do not benefit from the different approaches available today for increasing fertility as they are ineffective. Therefore, there is still a need to find new alternatives for improving natural reproductive efficiency and/or treating female infertility that provide greater efficacy.

DISCLOSURE OF THE INVENTION

It has now been found that the administration of a tungsten (VI) salt or a solvate of said salt is effective for treating infertility in a non-diabetic female mammal, for favoring normal reproduction and fertility in a non-diabetic female mammal, and for increasing the efficacy of assisted reproductive techniques applied to a mammal. Despite the fact that sodium tungstate was known to be able to partially reverse impairments in the reproductive function of diabetic female mice because it normalizes blood glucose levels, the possibility of sodium tungstate having an effect on the function of the female reproductive system in non-diabetic female mammals, being presented as a treatment for infertility and/or favoring normal reproduction and fertility in non-diabetic female mammals, has not been described nor suggested. The efficacy of the administration of a tungsten salt for treating infertility or for improving or normalizing fertility has now been demonstrated through an animal model, specifically IRS2-/- female mice, as reflected in the examples of the present invention. An effect of tungsten salts on embryo implantation has also been demonstrated in the same animal model indicated above, as well as a positive effect on endometrial embryonic adhesion, based on an in vitro assay, the results of which also indicated in the examples.

Therefore, a first aspect of the present invention relates to a tungsten (VI) salt or a solvate thereof, for use thereof for the treatment of infertility in a non-diabetic female mammal or for favoring normal reproduction and fertility in a non-diabetic female mammal.

A second aspect of the present invention relates to a composition comprising a tungsten (VI) salt or a solvate thereof at a concentration greater than 100 mg/kg, as well as at least one pharmaceutically or dietetically acceptable excipient or vehicle, for the treatment of infertility in a non-diabetic female mammal or for favoring normal reproduction and fertility in a non-diabetic female mammal.

A third aspect of the invention relates to the use of a tungsten (VI) salt or a solvate thereof, as defined above, for the preparation of a medicinal product for the treatment of infertility in a non-diabetic female mammal or for favoring fertility in a non-diabetic female mammal.

A fourth aspect of the invention relates to a method for the treatment of infertility or for favoring normal reproduction and fertility in a non-diabetic female mammal, which comprises administering a therapeutically effective amount of a tungsten (VI) salt or a solvate thereof, as defined above.

DETAILED DISCLOSURE OF THE INVENTION

As indicated above, according to a first aspect the present invention relates to a tungsten (VI) salt or a solvate thereof, for the treatment of infertility in a non-diabetic female mammal or for favoring and/or contributing to normal reproduction and fertility in a non-diabetic female mammal.

The term "favoring normal reproduction and fertility" or "contributing to normal reproduction and fertility" refers to contributing to normal reproduction and fertility or improving normal reproduction and fertility (reducing the times for achieving pregnancy), "normal reproduction and fertility" being understood as a state of fertility in which pregnancy is achieved following the definitions provided above:

in a subfertility situation: pregnancy is achieved in a period of 12 months of regular, unprotected sexual intercourse; and in an infertility situation: pregnancy is achieved after a period 12 months of regular, unprotected sexual intercourse. The need to restore and/or promote ovulation, improve oocyte and embryo quality, increase zygote implantation on the uterine wall, regulate hypothalamic-pituitary-ovarian axis impairment, including polycystic ovarian syndrome, metabolic syndrome, hyperprolactinemia, endometriosis, hypothyroidism, multiple sclerosis, rheumatoid arthritis, lupus erythematosus, cirrhosis, rheumatoid arthritis, celiac disease, chronic kidney failure, idiopathic causes and eating disorders, such as anorexia nervosa and bulimia are included herein.

In the context of the present invention, the term "assisted reproductive technique" encompasses any assisted reproductive technique or artificial insemination, being understood as a group of biomedical techniques or methods facilitating or replacing at least one of the natural processes taking place during reproduction. They include, but are not limited to, induction of ovulation, artificial insemination (including insemination with donor's sperm) and in vitro insemination (including insemination of a donor's ovum or insemination with donor's sperm). Therefore, the assisted reproductive technique can be applied due to causes of infertility or reduced fertility, both in a female mammal (as defined above) and in a male mammal (for example, alterations of spermatozoids reflected in a seminogram, such as alterations of spermatozoid mobility, alterations of spermatozoid vitality, as well as alterations of spermatozoid morphology). The assisted reproductive technique can also be applied in women who, despite not having any fertility problem per se, must resort to the technique for various reasons, for example (but not limited to), women without a partner who require sperm donation, couples who have to resort to ovum and/or sperm donation due to genetic or another type of incompatibilities, or livestock that require embryo transfer for improved productivity. These assisted reproductive techniques generally have a reduced success rate of less than 50% or even 40%. That is due to the fact that the use of assisted reproductive techniques has an inherent reduction in the efficiency of reproductive process. One of the main causes of this low reproductive efficiency with the use of assisted reproductive techniques relates to difficulties in the embryo adhesion and implantation process.

In the context of the present invention, the term "improving" in the expression "improving the efficacy of an assisted reproductive technique" refers to increasing the success rate of such assisted reproductive techniques. Therefore, if the success rate in the age range of the mammalian couple on which the assisted reproductive technique is applied was, according to previous statistics, 43%, for example, a higher rate from 44% would involve an improvement in the efficacy of such technique. This improvement is mainly due to favoring embryo adhesion and implantation as a result of administering tungsten (VI) salts.

Even though the assisted reproductive technique is applied due to an alteration in the fertility of the male mammal of the couple, by improving embryo adhesion and implantation, the tungsten (VI) salts will be administered at least to the female mammal. Alternatively, the tungsten (VI) salts can be administered to both the female mammal and the male mammal.

The mammal in the context of the present invention can be any mammal, including, but not limited to, humans, mice, rats, rabbits, dogs, cats, guinea pigs, hamsters, cows, horses, pigs, sheep, goats, etc. According to a particular embodiment, the mammal is a human.

According to another particular embodiment, said salt is administered in a daily dose between 0.001 mg and 1000 mg of tungsten (VI) salt per kg of body weight of the female mammal.

In another particular embodiment, the tungsten (VI) salt comprises a tungsten (VI) anion and a pharmaceutically or veterinary acceptable cation. "Pharmaceutically or veterinary acceptable cation" refers to any acceptable, non-toxic, organic or inorganic cation which is capable of forming a therapeutically effective tungsten (VI) salt and is suitable for use thereof in drug or veterinary therapy. The cation is preferably an alkaline or alkaline earth cation. The cation is more preferably selected from the group consisting of sodium, potassium, magnesium, calcium and zinc. According to a particular embodiment, the cation is sodium. According to another particular embodiment, the cation is zinc.

The tungsten (VI) anion in the tungsten (VI) salt is preferably selected from $WO_4^{2-}$, $HWO_4^-$, $W_2O_7^{2-}$ and $HW_2O_7^-$ ions. The anion is preferably $WO_4^{2-}$.

According to an additional particular embodiment, the solvate of the tungsten (VI) salt is a hydrate, more preferably a dihydrate.

All the features listed individually for different elements of the invention can be combined with one another, all the possible combinations being included within the scope of the present invention. For example, according to a preferred embodiment the solvate of the tungsten (VI) salt is a dihydrate and the cation is a sodium cation. Similarly, the rest of the possible combinations is also intended to be included within the scope of the present invention.

An additional aspect of the invention is a composition comprising a tungsten (VI) salt or a solvate thereof as defined above at a concentration equal to or greater than 100 mg/kg and at least one pharmaceutically, veterinary or dietetically acceptable excipient or vehicle, for the treatment of infertility in a non-diabetic female mammal, for favoring normal reproduction and fertility in a non-diabetic female mammal, or for increasing the efficacy of an assisted reproductive technique applied to a mammal.

The term "pharmaceutically, veterinary or dietetically acceptable excipient or vehicle" refers to excipients or vehicles suitable for use thereof in pharmaceutical, veterinary or food technologies for preparing the compositions. These components, excipients or carriers must be compatible with other ingredients of the composition. It must also be suitable for use thereof in contact with the tissue or organ of human beings and animals without excessive toxicity, irritation, allergic response or other immunogenicity problems or complications at a reasonable benefit/risk ratio. They are substances lacking pharmacological activity at the concentrations present in a pharmaceutical form. The excipients or vehicles are used to provide the pharmaceutical or veterinary form characteristics which assure the stability, bioavailability, acceptability and ease of administration of one or more active ingredients. As regards the extent to which the excipients affect active ingredient release, they will be able to modify the magnitude and the time profile of the pharmacological activity of the drug product, by means of changes in its bioavailability. The excipients are also used to provide the preparation with suitable form or consistency. Examples of types of excipients: solubilizers, disintegrants or disintegrating agents, emulsifiers (emulsifying agents), dyes, flavorings, binders, antioxidants, lubricants, preservatives, thickeners, etc.

According to a preferred embodiment, the excipient or vehicle is pharmaceutically or veterinary acceptable, and the composition is a pharmaceutical composition for the treatment of infertility in a non-diabetic female mammal or for increasing the efficacy of an assisted reproductive treatment applied to a mammal.

The pharmaceutical composition is preferably in the form of a pill, tablet, pastille, capsule, powder, wafer, effervescent powder or tablets, solution, suspension, syrup or granules.

According to another preferred embodiment, the composition is a food composition for favoring normal reproduction and fertility in a non-diabetic female mammal.

The food composition can be a liquid composition or beverage, a solid composition or a nutritional supplement or complement (also referred to as dietary or food supplement or complement). In the context of the present invention, the term "food composition" would encompass any solid or liquid food enriched with tungsten (VI) salt as well as any nutritional supplement or complement containing at least one tungsten (VI) salt.

The food composition can be a liquid composition, i.e., a beverage, according to terms most generally used in the society. In the context of the present invention, such liquid composition includes, but is not limited to, any beverage selected from the group consisting of animal or plant milk, as well as any derivative thereof, such as for example, milk shakes, yogurt, kefir, etc.; fruit and/or vegetable juices; still water or sparkling water, or flavored or sweetened (by means of nutritive sweeteners (sucrose, fructose . . . ) or artificial sweeteners) water or beverages; seasonings, such as for example, any salsa, dressing, ketchup, oil, vinegar or vinegar preparations; alcoholic beverages of any type; tea, coffee; as well as all types of refreshing beverages or soft drinks, or energizing beverages.

The food composition can also be a solid composition. Such solid composition can, for example, be selected from, but is not limited to, the group consisting of animal or plant milk derivatives, such as cheese, butter, margarine and tofu; any type of bread, including fresh, packaged or frozen bread, sliced bread, wholemeal bread, spiced bread, sweet bread, salty bread, etc; pasta prepared from any cereal flour, such as wheat or semolina flour (macaroni, spaghetti, noodles, etc); baked goods, including cakes, cookies, muffins, doughnuts, etc.; infusions, tea or coffee, in bulk or in sachets, for preparing beverages; jellies, candies, including gummy candies, better known as "soft fruit candies"; as well as any type of solid seasoning, for example, oregano, salt, coriander, parsley, basil, etc, or mixtures thereof.

Finally, the food composition can also be a nutritional, dietary or food supplement or complement, any of these terms being used in the context of the present invention in an equivalent manner. These terms are normally used for compositions consumed orally, which contain an ingredient intended for complementing the diet, in the case of the present invention, the tungsten (VI) salt/salts. They shall never replace a conventional food, or be the only component of a meal or of the diet. They can be found in different presentations, such as pastilles, pills, tablets, capsules, soft gelatin capsules, gelatin capsules, wafers, effervescent tablets, liquids (solution, suspension, syrup), granules and powders, all of which are included as particular embodiments within the scope of the present invention. Dietetically or pharmaceutically acceptable excipients are obvious for the skilled person for obtaining any of the preceding presentations, and they are included within the scope of the present invention.

According to a particular embodiment, any of the preceding compositions (pharmaceutical composition, solid composition, liquid composition or nutritional supplement/complement) comprises in their composition at least one nutritive sweetener, such as sucrose or fructose. Ingestion of these nutritive sweeteners must be controlled and limited in diabetic patients, therefore a food composition including such nutritive sweetener would be contraindicated in diabetic mammals or would at least be taken into account in controlling their diet.

According to a particular embodiment, the non-diabetic female mammal is selected from the group consisting of female mammals that require restoring and/or promoting ovulation, improving oocyte and embryo quality, increasing zygote implantation on the uterine wall, regulating hypothalamic-pituitary-ovarian axis impairment, including polycystic ovarian syndrome, metabolic syndrome, hyperprolactinemia, endometriosis, hypothyroidism, multiple sclerosis, rheumatoid arthritis, lupus erythematosus, cirrhosis, rheumatoid arthritis, celiac disease, chronic kidney failure, idiopathic causes and eating disorders, such as anorexia nervosa and bulimia.

According to another particular embodiment, the non-diabetic female mammal is selected from the group consisting of female mammals having insulin resistance (also known as resistance to insulin or insulinic resistance); when insulin resistance occurs together with hyperglycemia, it can lead to the development of diabetes, nevertheless insulin resistance alone does not lead to a diabetic condition. The female mammals having insulin resistance are preferably selected from the group consisting of female mammals having one or more of the following conditions: obesity or overweight, metabolic syndrome, prediabetes, polycystic ovarian syndrome, hypertension, heart disease, hyperlipidemias or dyslipidemia, hyperthyroidism, hyperparathyroidism, hyperleptinemia or leptin resistance, sedentary life style, eating disorders, obstructive sleep apnea syndrome, fetal malnutrition, Prader-Willi syndrome, Rabson-Mendenhall syndrome, fatty liver, leprechaunism, pathologies associated with excessive glucocorticoid secretion (e.g., acromegaly), insulin resistance caused by pharmacological treatments (e.g., glucocorticoids, thiazide diuretics, beta-blockers), stress or early menarche [Egas Béjar, Daniela et. al *Insulinorresistencia/Insulin resistance. Medicina (Guayaquil)*; 10(2):159-166, April 2005; Graves, Thomas K. WHY ISN'T THIS INSULIN WORKING? Western Veterinary Conference 2013 (SA113); Ximena Gaete V. *Adelanto de la pubertad en Chile y el mundo. Rev Chil Pediatr* 77 (5); 456-465, 2006; Leszek Szablewski *Glucose Homeostasis and Insulin Resistance* (eISBN: 978-1-60805-) Bentham e-books]. Many of these indications have been described to be unrelated to infertility, including prediabetes [*Acta Diab. Latina* 4, 507, 1967].

In the compositions of the invention, the salt or tungsten (VI) salts or a solvate thereof are present at a concentration of at least 100 mg/kg. According to particular embodiments, the salt or tungsten (VI) salts are comprised in the composition at concentrations of at least 150 mg/kg, at least 200 mg/kg, at least 250 mg/kg, at least 300 mg/kg, at least 350 mg/kg, at least 400 mg/kg, at least 450 mg/kg, at least 500 mg/kg, at least 550 mg/kg, at least 600 mg/kg, at least 650 mg/kg, at least 700 mg/kg, at least 750 mg/kg, at least 800 mg/kg, at least 850 mg/kg, at least 900 mg/kg or at least 850 mg/kg.

According to another particular embodiment, the total concentration of tungsten (VI) salts is equal to or less than 1000 mg/kg.

According to another particular embodiment, the food composition will be suitable for the administration of tungsten salts in a daily dose between 0.001 mg per kg of body weight of the female mammal (hereinafter, mg/kg/day) and the maximum tolerated dose for the corresponding female mammal species.

According to a more particular embodiment, the maximum daily dose will be 1000 mg/kg/day; according to additional particular embodiments, the administration would be carried out in doses of at least 0.001 mg/kg/day, at least 0.01 mg/kg/day, at least 0.1 mg/kg/day, at least 0.5 mg/kg/day, at least 1 mg/kg/day, at least 10 mg/kg/day, at least 25 mg/kg/day, at least 50 mg/kg/day, at least 100 mg/kg/day, at least 200 mg/kg/day, at least 300 mg/kg/day, at least 400 mg/kg/day, at least 500 mg/kg/day, at least 600 mg/kg/day, at least 700 mg/kg/day, at least 800 mg/kg/day or at least 900 mg/kg/day.

A third aspect of the invention relates to the use of a tungsten (VI) salt or a solvate thereof, as defined above, for the preparation of a medicinal product for the treatment of infertility in a non-diabetic female mammal or for favoring fertility in a non-diabetic female mammal.

A fourth aspect of the invention relates to a method for the treatment of infertility or for favoring normal reproduction and fertility in a non-diabetic female mammal, which comprises administering a therapeutically effective amount of a tungsten (VI) salt or a solvate thereof, as defined above.

All the definitions and preferred meanings provided above in relation to the first aspect of the invention are applicable to the other aspects of the invention. Therefore, for example, the tungsten (VI) salt will comprise a tungsten (VI) anion and a dietetically or pharmaceutically acceptable cation, which will preferably be an alkaline or alkaline earth cation, even more preferably a sodium, potassium, magnesium and calcium and zinc cation. Particularly, the salt will be tungsten (VI) sodium salt. The tungsten (VI) anion is once again selected from $WO_4^{2-}$, $HWO_4^-$, $WO_2O_7^{2-}$ and $HW_2O_7^-$ ions, preferably $WO_4^{2-}$, and in the case of being presented in the form of a solvate, the solvate will preferably be a hydrate, more specifically a dihydrate. The rest of the particular embodiments provided above for the first aspect also relate to other aspects.

A series of non-limiting, illustrative examples of the present invention are included below.

EXAMPLES

Example 1. Description of the Animal Model (IRS2−/− Female Mice)

The mouse model used for determining the activity of tungsten (VI) salts for favoring normal reproduction and fertility is an Irs2 gene knock-out mouse, IRS2$^{-/-}$[Burks et. al., "*IRS-2 pathways integrate female reproduction and energy homeostasis*", Nature, 2000, vol. 407, pp. 377-382]. Irs2 gene deletion translates into a clear sexual dimorphism in relation to fertility and carbohydrate metabolism.

The male mice of this model have insulin resistance and severe hyperglycemia that started at an early age. In contrast, the female mice remain relatively euglycemic at an early age and develop slight insulin resistance which remains until a later age (4-5 months). IRS2$^{-/-}$ female mice at an early age, about 10 weeks old, show a low follicular development and persistent anovulation, accompanied by the absence of estrous cycle in most mice. The pregnancy rate in IRS2$^{-/-}$ female mice is 9% compared to the rate of 100% in IRS$^{wt}$ (IRS-2$^{-/-}$ wild type) female mice. Given that female mice at these ages remain euglycemic and that they only develop slight insulin resistance, the profound impairment in fertility is not a direct result of anomalies in glucose metabolism.

The IRS2−/− female mice used are between 6 and 8 weeks of age. The publication by Burks et al, "*IRS-2 pathways integrate female reproduction and energy homeostasis*", *Nature*, 2000, vol. 407, pp. 377-382, describes that, while IRS2−/− male mice were already highly glucose intolerant at 6 weeks of age, IRS2−/− female mice maintained baseline glucose levels in the range of 120-160 mg/dl up to 4-5 months of age (page 378, column 1, end of the second paragraph). Additionally, the same publication describes that female mice of less than 10 weeks of age are relatively euglycemic and slightly insulin resistant. Therefore, the profound impairment in fertility in this animal model is not a direct result of an abnormal glucose metabolism in IRS-2-/- female mice. Baseline blood glucose levels of 120-160 mg/dl are considered normal levels ["Ciencia y Tecnologia en protección y experimentación animal", Ed McGraw-Hill/interamericana de España (2001). ISBN:84-486-0310-9 (page 27): the normal levels in mice are indicated between 63 and 176 mg/dl].

Other more recent studies performed with IRS2−/− mice have studied the mentioned differences existing between male and female mice; for example, *Biochemical Pharmacology* 2011, 81, 279-288, describes that the circulating insulin levels were not significantly different between wild type mice and IRS2−/− female mice and in response to several glucose concentrations, the response of IRS2−/− female mice in terms of insulin secretion was identical to that of control animals, wild type mice (page 281, column 2, paragraph 1; and page 284, column 2, paragraph 1 of the section entitled "Discussion"), whereas the insulin secretion in IRS2−/− male mice increased in comparison with the wild type controls.

Other studies conducted with this animal model have shown that IRS2 has critical and direct functions on the ovary, particularly in follicular development and ovulation, by means of regulating key components of the cell cycle mechanism that are involved in cell proliferation and differentiation coordination, clearly and directly linking the absence of IRS2 expression with infertility [Biology of Reproduction 2007, 76, 1045-1053].

The IRS2−/− animal model is primarily a beta-cell failure model [Am J Physiol Endocrinol Metab 2014, 306, E36-E47]. It describes that the progressive loss of beta cells due to the increased number of apoptotic beta cells determine the progression to diabetes in this animal model (see page E36, column 2, paragraph 2), only at advanced ages. The gradual reduction of beta cells is initially compensated for by a higher activity of persisting cells, and only in advanced ages, the decrease in the number of cells cannot be compensated for by the persisting cells, giving rise to the onset of hyperglycemia and the subsequent development of diabetes Fertility is a complex mechanism involving various factors. There is no "ideal" animal model, but rather many animal models, for example, those marketed by Jackson Laboratories (http://jaxmice.jax.org/list/ra861.html).

An important factor influencing fertility is the leptin hormone which is necessary both for fertility in males and females. The ovulation cycles in females are effected by leptin, and leptin levels out of the ideal range can have a negative effect on ovum quality. The IRS2−/− mice have high circulating leptin levels, which is probably another factor influencing fertility.

Therefore, this animal model covers a series of important infertility-related factors and is a suitable model for studying the efficacy of the compounds on infertility in female mammals.

Example 2. Ovulation, Implantation and Pregnancy Study

A. Animals

Ten IRS2$^{-/-}$ female mice of ages comprised between 6 and 8 weeks. Six "wild-type" (IRS2$^{wt}$) male mice of ages comprised between 6 and 8 weeks. The female and male mice were housed separately in normal conditions, i.e., a 12 h light/darkness cycle and controlled temperature and humidity. The animals were fed at will (also referred to as ad libitum) with a standard feed diet.

B. Method

Pre-Treatment Phase

After an acclimatization period, the IRS2$^{-/-}$ female mice were housed in groups of 4-6 mice/cage. Tungstate salt-free drinking water was administered to the animals during the pre-treatment phase (2 weeks).

Treatment Phase

Sodium tungstate was administered in the drinking water (ad libitum) by means of a solution of 2 mg/ml of sodium tungstate dihydrate (marketed by Carlo Erba) in distilled water after the pre-treatment phase (day 0 of treatment) and up to 4 weeks before sacrificing the animals. The daily dose of sodium tungstate ingested by the mice was about 180 mg/kg of body weight.

Cross-Breeding

After the first three weeks of treatment, the IRS2$^{-/-}$ female mice were housed in cages in pairs together with a IRS2$^{wt}$ male mouse continuously.

The mice were observed daily to look for signs of pregnancy or birth.

After 4 weeks, the male mice were exchanged between the cages and they were kept therein for another 4 weeks.

The administration of tungstate was maintained for 8 weeks in which male and female mice were housed together. After these 8 weeks, treatment was withdrawn and the male and female mice were housed together for 4 additional weeks.

Sacrifice

After this period, the female mice were sacrificed and biopsy was carried out to look for indications of pregnancy.

C. Results

Results of the Ovulation Study

During the pre-treatment period and during the first 3 weeks of treatment, vaginal smears were performed in 6 randomly chosen female mice on days −8; −5; −2; −1; 7; 8; 14; 15 and 22, to determine the phase of the estrous cycle they were in.

Between 1 and 2 ml of saline solution was introduced into the vagina of the mice with a Pasteur pipette. Vaginal exudate was collected with the same pipette and spread on a slide. Once air-dried, it was fixed and stained with the Papanicolau technique.

The Papanicolau technique comprises staining the vaginal smears fixed on the slide in the following manner:

10 immersions in 50% v/v alcohol;
Immersing in Harris hematoxylin solution for 3 minutes;
Rinsing with running water;
10 immersions in acid alcohol (1% hydrochloric acid);

Rinsing with running water;
10 immersions in 95% v/v alcohol;
Immersing in OG-6 solution for 30 seconds;
10 immersions in 96% v/v alcohol;
Immersing in eosin solution for 1 minute;
10 immersions in 96% v/v alcohol;
10 immersions in 86% v/v alcohol; and
10 immersions in xylol The preparations were analyzed by trained staff using a coding in a single-blind manner for eliminating observer bias.

The samples were identified in the following phases: diestrus, proestrus, estrus, metestrus, anestrus or non-evaluable. The cyclical nature of the four phases in periods of 4 to 6 days are indicative of a normal estrous cycle, whereas the absence of this cyclical nature and the persistence in anestrus, diestrus or proestrus phases are indicative of the absence of estrous cycle.

Of the 10 female mice subjected to study, Table 1 summarizes the phases of the estrous cycle in the vaginal smears performed in 6 of these IRS2$^{-/-}$ female mice.

TABLE 1

| Mouse | Time (days) | | | | | | | | |
|---|---|---|---|---|---|---|---|---|---|
| No. | −8 | −5 | −2 | −1 | 7 | 8 | 14 | 15 | 22 |
| 72 | A | A | P | D | E | E-M | E | E | A |
| 898 | D | P | P | P | E | E | E-M | M | M |
| 926 | D | D | P | P | E-M | E-M | D | E | P |
| 928 | D-P | D | P | P | E | E | E-M | M | A |
| 942 | A | D | P | P | E | E-M | E-M | A | D |
| 972 | D | D | — | P | M | M | — | D | D |

The phases of the estrous cycle are the following: A: Anestrus; D: Diestrus; P: Proestrus; E: Estrus; and M: Metestrus.

The phases of the estrous cycle found in the vaginal smears of the IRS2$^{-/-}$ female mice of Table 1 show that during the pre-treatment period all the mice were in the proestrus (P) or diestrus (D) phase, i.e., with the absence of estrous cycle.

However, after starting the administration of tungstate, it is observed that the IRS2$^{-/-}$ female mice are in the late phases of estrous cycle, i.e., estrus (E) and metestrus (M) phases, which is indicative of the recovery of a normal estrous cycle.

These results indicate that the administration of a tungsten (VI) salt allows quick recovery (on the seventh day of treatment) of the estrous cycle in infertile, non-diabetic IRS2$^{-/-}$ female mice in 100% of analyzed mice.

Results of the Implantation and Pregnancy Study

After the cross-breeding period of the method of section B, the female mice were sacrificed and biopsies were carried out to look for indications of pregnancy.

Table 2 summarizes the age at the time of treatment, whether or not there was pregnancy and the number of embryos per female mouse.

TABLE 2

| | Age (months) at the start of | | | Number of embryos |
|---|---|---|---|---|
| Mouse No. | treatment | cross-breeding | Pregnancy | implanted or young born |
| 72 | 10 | 12 | YES | 1 young |
| 942 | 10 | 12 | YES | 8 young |
| 928 | 10 | 12 | YES | 7 embryos |
| 931 | 10 | 12 | YES | 3 young |
| 898 | 10 | 12 | YES | 7 embryos |
| 900 | 10 | 12 | NO | — |
| 921 | 10 | 12 | YES | 6 embryos |
| 926 | 10 | 12 | YES | 8 young |
| 972 | 8 | 10 | NO | — |
| 973 | 8 | 10 | YES | 7 embryos |

The results of Table 2 show that while the pregnancy rate in untreated IRS2$^{-/-}$ female mice is 9%, the pregnancy rate in IRS2$^{-/-}$ female mice treated with tungstate increases to 80%.

Furthermore, these results also show that the mean of young/implanted embryos per pregnant female mouse is about 5, a number which can be considered comparable to the number of young of a female mouse.

Therefore, the results of Tables 1 and 2 demonstrate that tungsten (VI) salt is an effective treatment for recovering ovulation and/or increasing oocyte implantation. Therefore, the administration of a tungsten (VI) salt as defined in the present invention is effective for the treatment of infertility in non-diabetic female mammals.

Example 3. Glycemia and Body Weight Study

A. Animals

Six IRS2$^{-/-}$ female mice of ages comprised between 6 and 8 weeks.

The female mice were housed in normal conditions, i.e., a 12 h light/darkness cycle and controlled temperature and humidity. The animals were fed at will (also referred to as ad libitum) with a standard feed diet.

B. Method

Treatment Phase

After an acclimatization period, sodium tungstate was administered in the drinking water (ad libitum) by means of a solution of 2 mg/ml of sodium tungstate dihydrate (marketed by Carlo Erba) in distilled water after the pre-treatment phase (day 0 of treatment) and for 12 days.

C. Results

The body weight was monitored on days 0, 2, 5, 7, 9 and 12 of the treatment period, and the blood glucose was determined after 6 hours of fasting on each of the aforementioned days by means of drawing blood from the tail vein and with a glucose sensor (AccuTrend glucose sensor, Roche, Mannheim, Germany).

Table 3 summarizes the glycemic levels expressed in mg/dl, and Table 4 summarizes the body weight of the mice under study expressed in grams.

TABLE 3

| | Glycemia (mg/dl) | | | | | |
|---|---|---|---|---|---|---|
| | R1327 | R1345 | R1347 | R1354 | R1376 | R1381 | Average |
| Day 0 | 146 | 129 | 115 | 126 | 141 | 112 | 128,17 |
| Day 2 | 136 | 128 | 118 | 110 | 105 | 107 | 117,33 |
| Day 5 | 125 | 142 | 114 | 111 | 137 | 105 | 122,33 |

TABLE 3-continued

| | Glycemia (mg/dl) | | | | | | |
|---|---|---|---|---|---|---|---|
| | R1327 | R1345 | R1347 | R1354 | R1376 | R1381 | Average |
| Day 7 | 140 | 110 | 106 | 89 | 133 | 135 | 118,83 |
| Day 9 | 125 | 153 | 109 | 108 | 131 | 125 | 125,17 |
| Day 12 | 136 | 116 | 111 | 86 | 123 | 141 | 118,83 |

TABLE 4

| | Body weight (g) | | | | | | |
|---|---|---|---|---|---|---|---|
| | 1327 | 1345 | 1347 | 1354 | 1376 | 1381 | Average |
| Day 0 | 22.7 | 15.33 | 18.21 | 16.5 | 13.99 | 15.45 | 17.03 |
| Day 2 | 22.9 | 14.84 | 18.98 | 17.01 | 14.18 | 16.04 | 17.33 |
| Day 5 | 22.61 | 14.89 | 18.2 | 16.61 | 13.79 | 15.72 | 16.97 |
| Day 7 | 22.42 | 15.07 | 17.81 | 16.35 | 13.74 | 15.66 | 16.84 |
| Day 9 | 22.85 | 15.56 | 17.9 | 16.89 | 14.5 | 16.39 | 17.35 |
| Day 12 | 23.15 | 15.91 | 18.24 | 17.19 | 14.92 | 16.89 | 17.72 |

The results of Tables 3 and 4 show that during the administration of sodium tungstate no variations were observed in the body weight or in the glycemia in the first 12 days of treatment, the same period in which ovulation is successfully re-established in the tested female mice from day 7 of treatment (cf. Table 1).

Therefore, the results of Tables 1 to 4 demonstrate that a tungsten (VI) salt is a treatment effective for recovering ovulation and/or increasing oocyte implantation, regardless of the changes in body weight and in carbohydrate metabolism. It is therefore demonstrated that the administration of a tungsten (VI) salt as defined in the present invention or a composition containing such tungsten (VI) salt has a direct effect on the female reproductive system and is therefore effective for favoring normal reproduction and fertility in non-diabetic female mammals.

Example 4. Endometrial Embryonic Adhesion Study

A. Model

An "in vitro" human-human embryonic adhesion model made up the HEC1-A endometrial cell line and the JEG-3 trophectoderm cell line was used to determine the effect of sodium tungstate on endometrial receptivity.

The use of in vitro models, and specifically the model based on the mentioned cell lines (HEC-1A and JEG-3), is considered a standard model for studying endometrial receptivity and particularly the adhesion the trophoblast to the endometrium (Fertility and Sterility 2011; 96, 522-529; Methods in Enzymology 2006; 420:3-18 or FASEB J. 201; 26:3715-3727).

The JEG-3 cell line which simulates the trophectoderm cells of a human embryo are cells that grow in monolayers in laboratory using low adherence plates and are capable of forming spheroids simulating the human embryo; this is one of the most widely used cell lines for conducting in vitro embryonic adhesion assay.

B. Method

The cell lines were commercially purchased (American Type Culture Collection (ATCC); Rockville, Md., USA) for conducting the endometrial embryonic adhesion experiments. They were thawed and expanded in 4 passes for obtaining sufficient cells to perform all the assays.

The HEC1-A cells were plated in 24-well plates and cultured with McCoy 5A culture medium supplemented with 10% fetal bovine serum and 0.1% antibiotics (fungizone and penicillin), until reaching 90% confluence. After reaching the confluence, there was added to the culture medium sodium tungstate at a final concentration of 10 µM, as well as Withaferin A (as a control, a compound that prevents embryonic adhesion) or culture medium (baseline adhesion data), without any additional component, for 24 hours.

The JEG-3 cells were plated in low adherent plates with Eagle's minimal essential medium (EMEM) culture medium supplemented with 10% fetal bovine serum and 0.1% antibiotics (fungizone and penicillin). Twenty-four hours before the adhesion assay, the JEG-3 trophoblast spheroids were formed from this culture. To that end, JEG-3 cells in the medium described above were suspended in an Erlenmeyer flask under stirring at a concentration of $6 \times 10^5$ cells/6 ml. The resulting spheroids were collected for the adhesion assay.

For the adhesion assay, 24 hours after culturing the HEC-1A cells with culture medium adding sodium tungstate, Withaferin A or without adding any treatment, the culture medium was changed with fresh culture medium without treatments under study. The trophectoderm spheroids were added onto the monolayer of HEC-1A cells, placing 6 to 10 spheroids per well. The adhesion of the spheroids was measured after 60 minutes, counting spheroid that was floating in the culture medium as non-adhered spheroid and spheroid that was not floating as adhered spheroid. The examination was conducted with an inverted microscope (Nikon Diaphot 300; Nikon Corp., Tokyo, Japan). The assay was conducted in triplicate.

C. Results

The results obtained are listed in Table 5. A higher percentage of embryonic adhesion was observed in the conditions in which the HEC-1A lines were treated with sodium tungstate with respect to those in which they were not treated. No adhesion whatsoever is observed in cells treated with the negative control (C−), Withaferin A.

TABLE 5

| | Absolute adhesion rates | | | |
|---|---|---|---|---|
| | Exp 1 | Exp 2 | Exp 3 | Mean |
| Baseline adhesion | 12% | 48% | 31% | 30% |
| 10 µM sodium tungstate | 31% | 65% | 35% | 44% |
| Withaferin A (C—) | 0% | 0% | 0% | 0% |

Particular Compositions of the Invention

Food compositions according to the invention are prepared below in an illustrative manner. They must in no way be interpreted as limiting the scope of the invention.

Example 5

A tungsten salt-enriched salad dressing is prepared. An amount of 25 mg of $Na_2WO_4$ (100 mg/kg) is added to 250 grams of a commercially available dressing and it is mechanically stirred for 30 minutes.

Example 6

A tungsten salt-enriched ketchup-type salsa is prepared. To that end, 170 mg of $CaWO_4$ are added to 200 grams of commercially available ketchup and it is mechanically stirred for 1 hour.

Example 7

A tungsten salt-enriched milk is prepared. To that end, 1 kg of whole cow's milk is provided, 150 mg of $ZnWO_4$ are added and it is mechanically stirred for 20 minutes. It is recommended to shake the packaging immediately before consumption.

Example 8

A tungsten salt-enriched fruit juice is prepared. Five-hundred mg of $MgWO_4$ are added to 1 kg of commercial juice and it is mechanically stirred for 10 minutes. It is recommended to shake the packaging immediately before consumption.

Example 9

Coated tablets with the following composition are prepared:
PH200 Microcrystalline cellulose (diluent/gliding agent) 250.00 mg
Colloidal anhydrous silica (gliding agent/adsorbent) 3.00 mg
Magnesium stearate (lubricant) 5.00 mg
Talc (lubricant) 7.00 mg
Opadry® white (Opadry® and-1-7000 White)(*) (coating film) 8.00 mg
Sodium tungstate dihydrate 200.00 mg
(*) mixture of hydroxypropylmethylcellulose, polyethylene glycol 6000 and titanium dioxide (E-171)

Example 10

Effervescent tablets with the following composition are prepared:
Sorbitol, aspartame, sucralose and xylitol (sweeteners) 0.025 mg per 10 mg
Calcium carbonate 0.350 mg per 10 mg
Citric acid (acidulant) 0.650 mg per 10 mg
Sodium acid carbonate (acidity regulator) 0.350 mg per 10 mg
Orange flavoring 0.25 mg per 10 mg
Tungsten salt

Example 11

Gelatin capsules with the following composition are prepared:
Nifedipine 6 mg
Xanthan gum 5 mg
Orange flavoring 0.3 mg
Citric acid 0.4 mg
Gelucire 44/14 90 mg
PH10 microcrystalline cellulose (diluent) 92.00 mg/capsule
Sodium tungstate dihydrate 100.00 mg/capsule

The invention claimed is:

1. A method for favoring normal reproduction and fertility or for increasing efficacy of an assisted reproductive technique in a non-diabetic female mammal, said method comprising administering to said mammal tungsten (VI) salt, or a solvate thereof;
wherein said salt is administered at a daily dose of between 0.001 mg and 1000 mg of the tungsten (VI) salt per kg of body weight of the mammal;
wherein said mammal is not infertile,
wherein the normal reproduction and fertility is a state of fertility in which pregnancy is achieved in a period of 12 months of regular, unprotected sexual intercourse; and
wherein the assisted reproductive technique is selected from a technique comprising induction of ovulation, artificial insemination or in vitro fertilization;
such that the normal reproduction and fertility in said mammal is favored or the efficacy of said assisted reproductive technique in said mammal is increased.

2. The method according to claim 1, wherein the mammal is a human.

3. The method according to claim 1, wherein said salt comprises a tungsten (VI) anion and a pharmaceutically, veterinary or dietetically acceptable cation.

4. The method according to claim 1, wherein the cation is an alkaline or alkaline earth cation.

5. The method according to claim 4, wherein the cation is selected from the group consisting of sodium, potassium, magnesium, calcium and zinc.

6. The method according to claim 5, wherein the cation is sodium.

7. The method according to claim 5, wherein the cation is zinc.

8. The method according to claim 3, wherein the tungsten (VI) anion is selected from the group consisting of $WO_4^{2-}$, $HWO_4^-$, $W_2O_7^{2-}$ and $HW_2O_7^-$ ions.

9. The method according to claim 8, wherein the anion is $WO_4^{2-}$.

10. The method according to claim 1, wherein the solvate is dihydrate.

11. A method for favoring normal reproduction and fertility or for increasing efficacy of an assisted reproductive technique in a non-diabetic female mammal, said method comprising administering to said mammal a composition comprising a tungsten (VI) salt or a solvate thereof and at least one pharmaceutically, veterinary or dietetically acceptable excipient or vehicle, wherein said mammal is not infertile, such that the normal reproduction and fertility in said mammal is favored or the efficacy of said assisted reproductive technique in said mammal is increased, wherein the tungsten (VI) salt or a solvate thereof is present in said composition at a concentration equal to or greater than 100 mg of the tungsten (VI) salt or a solvate thereof per kg of the composition;
wherein the normal reproduction and fertility is a state of fertility in which pregnancy is achieved in a period of 12 months of regular, unprotected sexual intercourse; and
wherein the assisted reproductive technique is selected from a technique comprising induction of ovulation, artificial insemination or in vitro fertilization.

12. The method according to claim 11, wherein the method is for increasing efficacy of an assisted reproductive technique in a mammal, and wherein the excipient or vehicle is pharmaceutically or veterinary acceptable.

13. The method according to claim 11, wherein the composition is in the form of a pill, a tablet, a pastille, a capsule, a powder, a wafer, an effervescent powder or a tablet, a solution, a suspension, a syrup or a granule.

14. The method according to claim 11, wherein the method is for favoring normal reproduction and fertility in a non-diabetic female mammal, wherein said composition is a food composition.

15. The method according to claim 14, wherein said composition is a liquid composition or a beverage.

16. The method according to claim 14, wherein said composition is a solid composition.

17. The method according to claim 14, wherein said food composition is a nutritional supplement or complement.

18. The method according to claim 11, wherein said composition comprises sucrose.

* * * * *

UNITED STATES PATENT AND TRADEMARK OFFICE
CERTIFICATE OF CORRECTION

PATENT NO. : 10,376,540 B2
APPLICATION NO. : 15/327292
DATED : August 13, 2019
INVENTOR(S) : Ignacio Canals Almazán et al.

It is certified that error appears in the above-identified patent and that said Letters Patent is hereby corrected as shown below:

On the Title Page

At Column number 1, (73) Assignee:, delete "OXOLIKE, S.L." and replace it with --OXOLIFE, S.L.--

Signed and Sealed this
First Day of October, 2019

Andrei Iancu
*Director of the United States Patent and Trademark Office*